(12) United States Patent
Law et al.

(10) Patent No.: US 8,556,529 B2
(45) Date of Patent: Oct. 15, 2013

(54) APPLICATORS

(75) Inventors: Brian Robert Law, Leicester (GB); David John Pritchett, Ashby de la Zouch (GB)

(73) Assignee: Rieke Corporation, Auburn, IN (US)

( * ) Notice: Subject to any disclaimer, the term of this patent is extended or adjusted under 35 U.S.C. 154(b) by 0 days.

(21) Appl. No.: 13/369,848

(22) Filed: Feb. 9, 2012

(65) Prior Publication Data

US 2012/0219346 A1 Aug. 30, 2012

Related U.S. Application Data

(63) Continuation of application No. PCT/GB2010/001521, filed on Aug. 10, 2010.

(30) Foreign Application Priority Data

Aug. 10, 2009 (GB) .................................. 0913972.6

(51) Int. Cl.
*B43K 5/14* (2006.01)

(52) U.S. Cl.
USPC ............................. 401/133; 401/132; 401/263

(58) Field of Classification Search
USPC .............. 401/132–135, 176, 264, 263, 40–43
See application file for complete search history.

(56) References Cited

U.S. PATENT DOCUMENTS

| | | | |
|---|---|---|---|
| 2,976,560 A | 3/1961 | Turner | |
| 2,998,822 A | 9/1961 | Birch et al. | |
| 3,324,855 A | 6/1967 | Heimlich et al. | |
| 3,349,966 A * | 10/1967 | Schwartzman | 222/80 |
| 3,399,020 A | 8/1968 | Margolis et al. | |
| 3,519,364 A | 7/1970 | Truhan | |
| 3,601,287 A | 8/1971 | Schwartzman | |
| 3,636,922 A | 1/1972 | Ketner | |
| 3,891,331 A | 6/1975 | Avery | |

(Continued)

FOREIGN PATENT DOCUMENTS

| | | |
|---|---|---|
| DE | 20 2005 012686 U1 | 10/2005 |
| WO | WO 85/04794 A1 | 11/1985 |

(Continued)

OTHER PUBLICATIONS

International Search Report and Written Opinion for WO 2011/018621 dated Mar. 29, 2011.

(Continued)

*Primary Examiner* — David Walczak
(74) *Attorney, Agent, or Firm* — Woodard Emhardt Moriarty McNett & Henry LLP

(57) ABSTRACT

An applicator includes an applicator body, an applicator pad attached at a front part of the applicator body, and a pre-loaded container of liquid received in \ the applicator body. The applicator body defines a flow path from the container to the applicator pad. The container includes a front closure portion which is openable to allow liquid to flow from the container into the flow path. The applicator body has a structure which interacts with the front of the container when the container is moved to an opening position relative to the applicator body to open the openable front closure portion. Wherein the container defines a front chamber and a rear chamber with a liquid-impermeable intermediate barrier therebetween. Wherein the container includes a longitudinal pusher element extending relatively movably between the ends of the front chamber.

29 Claims, 12 Drawing Sheets

(56) References Cited

U.S. PATENT DOCUMENTS

| | | |
|---|---|---|
| 4,084,910 A | 4/1978 | LaRosa |
| 4,140,409 A | 2/1979 | DeVries |
| 4,148,318 A | 4/1979 | Meyer |
| 4,173,978 A | 11/1979 | Brown |
| 4,183,684 A | 1/1980 | Avery, Jr. |
| 4,201,491 A | 5/1980 | Kohler |
| 4,225,254 A | 9/1980 | Holberg et al. |
| 4,415,288 A | 11/1983 | Gordon et al. |
| 4,498,796 A | 2/1985 | Gordon et al. |
| 4,507,111 A | 3/1985 | Gordon et al. |
| 4,578,055 A | 3/1986 | Fischer |
| 4,863,422 A | 9/1989 | Stanley |
| 4,925,327 A | 5/1990 | Wirt |
| 5,006,004 A | 4/1991 | Dirksing et al. |
| 5,015,228 A | 5/1991 | Columbus et al. |
| 5,019,033 A | 5/1991 | Geria |
| 5,088,849 A | 2/1992 | Johnson et al. |
| 5,147,337 A | 9/1992 | Plone |
| 5,288,159 A | 2/1994 | Wirt |
| 5,308,180 A | 5/1994 | Pournoor et al. |
| 5,435,660 A | 7/1995 | Wirt |
| 5,445,462 A | 8/1995 | Johnson et al. |
| 5,489,280 A | 2/1996 | Russell |
| 5,509,744 A | 4/1996 | Frazier |
| 5,568,988 A | 10/1996 | Knox et al. |
| 5,658,084 A | 8/1997 | Wirt |
| 5,713,843 A | 2/1998 | Vangsness |
| 5,769,552 A | 6/1998 | Kelley et al. |
| 5,775,826 A | 7/1998 | Miller |
| 5,791,801 A | 8/1998 | Miller |
| 5,871,297 A | 2/1999 | Rogers et al. |
| 5,908,256 A | 6/1999 | Bernstein |
| 5,934,296 A | 8/1999 | Clay |
| 6,190,367 B1 | 2/2001 | Hall |
| 6,238,117 B1 | 5/2001 | Griebel et al. |
| 6,371,675 B1 | 4/2002 | Hoang et al. |
| 6,422,778 B2 | 7/2002 | Baumann et al. |
| 6,471,095 B1 | 10/2002 | Cann |
| 6,475,701 B2 | 11/2002 | Ohno et al. |
| 6,488,665 B1 | 12/2002 | Severin et al. |
| 6,505,985 B1 | 1/2003 | Hidle et al. |
| 6,533,484 B1 | 3/2003 | Osei et al. |
| 6,536,975 B1 | 3/2003 | Tufts |
| 6,595,696 B1 | 7/2003 | Zellak |
| 6,616,363 B1 | 9/2003 | Guillaume et al. |
| 6,672,784 B2 | 1/2004 | Baumann et al. |
| 6,689,103 B1 | 2/2004 | Palasis |
| 6,729,786 B1 | 5/2004 | Tufts et al. |
| 6,743,211 B1 | 6/2004 | Prausnitz et al. |
| 6,755,586 B1 | 6/2004 | Frazier |
| 6,773,193 B2 | 8/2004 | Delage |
| 6,805,682 B1 | 10/2004 | Campbell |
| 6,811,341 B2 | 11/2004 | Crane |
| 6,869,242 B2 | 3/2005 | May |
| 6,909,339 B2 | 6/2005 | Yonekura et al. |
| 6,910,822 B2 | 6/2005 | Hidle et al. |
| 6,916,133 B2 | 7/2005 | Hoang et al. |
| 6,916,137 B2 | 7/2005 | Shiraiwa |
| 6,991,394 B2 | 1/2006 | Tufts et al. |
| 7,090,422 B2 | 8/2006 | Baumann et al. |
| 7,201,525 B2 | 4/2007 | Mohiuddin |
| 7,261,701 B2 | 8/2007 | Davis et al. |
| 7,866,907 B2 | 1/2011 | Cable, Jr. et al. |
| 8,002,486 B1 | 8/2011 | Tran |
| 8,113,731 B2 | 2/2012 | Cable, Jr. et al. |
| 8,348,537 B2 | 1/2013 | Cable, Jr. et al. |
| 2001/0055511 A1 | 12/2001 | Baumann et al. |
| 2002/0076255 A1 | 6/2002 | Hoang et al. |
| 2002/0076258 A1 | 6/2002 | Crosby et al. |
| 2003/0049069 A1 | 3/2003 | Osei et al. |
| 2003/0060746 A1 | 3/2003 | Mark |
| 2003/0068190 A1 | 4/2003 | Hidle et al. |
| 2003/0118629 A1 | 6/2003 | Scholz et al. |
| 2003/0149106 A1 | 8/2003 | Mosbey et al. |
| 2003/0194447 A1 | 10/2003 | Scholz et al. |
| 2004/0068218 A1 | 4/2004 | Davis et al. |
| 2004/0114988 A1 | 6/2004 | Baumann |
| 2004/0162533 A1 | 8/2004 | Alley |
| 2004/0179888 A1 | 9/2004 | Tufts et al. |
| 2004/0240927 A1 | 12/2004 | Hoang et al. |
| 2004/0267182 A1 | 12/2004 | Davis et al. |
| 2006/0039742 A1 | 2/2006 | Cable et al. |
| 2006/0072962 A1 | 4/2006 | Cybulski et al. |
| 2007/0147947 A1 | 6/2007 | Stenton |

FOREIGN PATENT DOCUMENTS

| | | |
|---|---|---|
| WO | WO 94/13352 A1 | 6/1994 |
| WO | WO 95/03734 | 2/1995 |
| WO | WO 99/51184 A1 | 10/1999 |
| WO | WO 00/10889 | 3/2000 |
| WO | WO 02/49708 A2 | 6/2002 |
| WO | WO 2004/062709 | 7/2004 |

OTHER PUBLICATIONS

International Search Report and Written Opinion for WO 2011/018622 dated Jan. 27, 2011.

* cited by examiner

APPLICATORS

CROSS REFERENCE TO RELATED APPLICATION

This application is a continuation of International Application No. PCT/GB2010/001521 filed Aug. 10, 2010 which claims the foreign priority benefit of GB 0913972.6 filed Aug. 10, 2009, both of which are hereby incorporated by reference.

BACKGROUND

This invention is directed to applicators for liquids and liquid reservoir containers for such applicators. It is particularly but not exclusively concerned with applicators for applying surgical prep liquids to the skin.

The conventional preparation of a patient's skin for surgery includes an extended period of cleaning using soap or the like, followed by the application of an antiseptic or disinfectant solution.

The oldest—and still widespread—method of applying the disinfectant is by dipping a swab, sponge or pad, held in forceps, into a dish of liquid and wiping it over the skin. Spent swabs/pads are continually discarded and fresh ones taken. The disinfectant ("pre-prep solution") is usually alcohol-based and may contain ingredients such as iodine that irritate or burn the skin. Moreover surgical prep is often done under severe time pressure and subject to safety and effectiveness there is every interest in doing it as quickly as possible.

Over the years many proposals have been made for hand-held applicator devices for applying surgical prep solution, incorporating an applicator head with a pad, sponge or other soft or deformable permeable element to be wiped across the skin, and a reservoir of the surgical prep solution—usually contained in a handle of the device—communicating with the applicator pad to feed solution. This can make the application more efficient by avoiding the repeated dipping and the discarding and replacement of spent swabs. By providing the solution in a sealed sterile vial, ampoule or cartridge, which can be opened inside the device by engaging it appropriately with an opening structure in the applicator body (e.g. a spike or cutter built into the applicator body to rupture a membrane or film closure on the front of the cartridge, or an oblique shoulder to break off the tip of a glass vial) operation of these devices can be neater and easier than swabs.

Surgical prep solutions are desirably coloured or dyed, to show where the solution has been applied. This presents a problem with pre-loaded containers for applicators, because usually the dye additive cannot be included in the solution pre-packaged in the container. Dye compounds have a tendency to interact chemically, degrading both themselves and the disinfectant over time. Moreover they may be unable to withstand the sterilisation conditions needed for the main disinfectant solution. So, dye must be provided separately in the applicator.

U.S. Pat. No. 7,241,065 uses a porous plug impregnated with dye and positioned in the applicator in front of the solution ampoule. Disinfectant solution from the ampoule is coloured as it flows through the plug on the way to the applicator pad. Another proposal provides a solid dye powder on the back of the applicator pad. These proposals may bring assembly problems, and the mixing of dye and disinfectant is likely to be non-uniform over the dispensing lifetime of the applicator.

The issue exists not only for dyes, since there may be other additives or components which could desirably be included in a liquid applied by an applicator using a pre-loaded liquid container, but which for various reasons, such as those mentioned above, cannot be pre-mixed in the pre-loaded liquid. This can apply to solid or liquid additives.

The present application presents new proposals or embodiments for applicators using pre-loaded liquid containers, and for new kinds of pre-loaded container for use with such applicators, addressing the above issues.

SUMMARY

The focus of the present disclosure is directed to a liquid applicator such as a surgical prep applicator having an applicator pad at a front part of the applicator attached to an applicator body including a structure for receiving a pre-loaded container of liquid, and defining a flow path for liquid to flow from the container to the applicator pad.

Usually the container will be discrete and received at or in a receiving structure of the applicator body, although it may be shipped in situ. The container has an openable front closure portion which when opened allows liquid to flow from the container into the flow path.

An opening means is provided for opening the front closure portion of the container. Preferably this opening means is provided by structure—typically fixed structure—of the applicator body which interacts directly with the front of the container received there, e.g. a cutter, spike or other penetrating protrusion or projection which pushes into or against the front of the container when the container is moved to an opening position e.g. by pushing the container into or onto the applicator body.

The corresponding openable structure of the container may be a film, foil or other layer that is cut, broken or ruptured, a frangible part which is broken away (as in the known use of glass vials whose front ends are broken off), or a displaceable wall part such as a partition or plug which can be moved (e.g. broken out, swung or slid) out of its position to create an opening for forward flow. The use of a displaceable piston or plug-type closure is novel and is an independent proposal herein.

Alternatively, although this is less preferred, the opening means may be provided at the side or rear of the container, or may indeed be incorporated as part of the container structure, but in any event is operable to open the openable front closure portion of the container e.g. by pushing or cutting through it from behind or from inside.

One proposal is that the container is provided having two chambers, a front chamber and a rear chamber, with a liquid-impermeable barrier or partition between them. The front chamber has the openable front portion leading into the applicator flow path. The applicator is operable to open the intermediate barrier between the front and rear chambers to allow mixing of first and second respective materials contained in them, at least one and preferably both of which are liquids. The first and second chambers are disposed in series in relation to the flow path, so that in use both the first and second materials pass into the applicator flow path through the openable front structure.

The first and second chambers may be housed or provided in a single main container body, the barrier between them being provided by an intermediate partition. One chamber may be provided as an insert fitted into a mouth of an outer container which also defines the other chamber. Desirably the insert chamber is self-contained, e.g. including the intermediate partition as part of its structure so that it can be filled with its respective material before fitting to the outer container. Preferably the insert chamber is at the front of the container arrangement so that its front opening is, or coincides with, the openable front structure. Preferably one of the chambers is smaller and contains an additive for a main liquid which is in the other, larger chamber. Preferably the smaller chamber is at the front.

The skilled person will understand that by providing enclosed chambers in series, difficulties associated with loose or exposed additive material such a dye can be avoided. Liquid additives can be used. Also it becomes possible to handle these separately, e.g. for a sterilisation process, if one chamber such as an insert chamber is self-contained. When liquid from a rear chamber flows through a front chamber, there is moreover a good opportunity for mixing of liquid and additive.

At a simple level these advantages can be obtained with opening means of a generally known type. For example a simple elongate cutter, spike or prong device in the applicator body may pass through, and open, both the front closure portion and the intermediate barrier which separates the first and second chambers. However we propose herein more sophisticated opening arrangements for the first and second chambers which provide for flexibility in the relative volumes, shapes, handling and assembly of these chambers without requiring extreme formations or movements for the opening operation.

In particular, the present disclosure describes a construction in which, in a said chamber having the intermediate barrier or partition at one end and the openable front closure portion at the other end, one or more longitudinal pusher elements extends inside the chamber relatively moveably between these ends. Either of the respective ends of the pusher structure may be integral with, or discrete from but adjacent to, the corresponding closure, barrier or actuating element at that end.

The principle is that an operating movement applied at one end, e.g. the action of a cutter, spike or pusher opening a closure at that end, is transmitted to the other end by a follower action of the internal pusher element(s) whereby it operative to open the intermediate barrier or partition without the operating movement needing to be large.

The preferred structure of this internal pusher or follower arrangement depends on the nature of the closures at either end of the chamber concerned. Preferably this feature is embodied in a self-contained insert chamber as mentioned above. If the intermediate closure is a rupturable layer e.g. film or foil, the pusher or follower has an end with a cutter, spike or the like protrusion to rupture it. If the intermediate closure is a plug, flap or piston which is opened by being pushed out of an opening, in which it fits sealingly, into a space beyond, then the pusher or follower structure may be designed simply to push on this or—especially in the case of a piston or plug structure—be formed fixed to or integral with it. The latter options have the advantage that the longitudinal alignment of the pusher or follower structure in the chamber is then naturally maintained.

As regards the structure at the other end of the chamber (i.e. remote from the intermediate closure, typically at the front), this also may be any of a rupturable layer or displaceable wall portion e.g. film, foil, plug, flap or piston as mentioned. The opening means on the applicator body is adapted accordingly. Usually the opening means operates by the front of the container being pushed into engagement with a projecting formation of the opening means through an operating stroke (distance). Over this operating stroke the opening means formation also pushes the pusher element(s)—either directly or via part of the front closure—to open the intermediate closure too.

The relative timing of the openings of the front closure and of the intermediate closure can be adjusted by the mechanism used. However we particularly prefer a mechanism which opens the intermediate closure at an intermediate stage of the operating stroke, before the front closure is opened. This gives an opportunity for mixing of the first and second materials before they flow out of the container. More especially we prefer that means are provided for arresting or interrupting the actuating movement stroke at the intermediate stage to give time for this mixing to take place.

This may be e.g. by a stepped formation of a path or track, on one of the container and the receiving part of the applicator body, for a projection on the other. The path or track can be formed with an intermediate abutment which meets the projection to interrupt the operating stroke—which is typically a direct push—at the intermediate point, and which can then be overcome or avoided to complete the stroke e.g. by a lateral or turning movement of the container relative to the body.

In one embodiment the closures at both ends of an insert chamber are provided by plug formations connected by one or more longitudinal members constituting the mentioned pusher or follower structure, so that when the plug at the front end is pushed in, the plug at the rear end is pushed out. This closure and pusher structure can be contained in an insert shell which also provides or supports the front and rear sealing seats for the plugs.

To provide the above-mentioned two-stage opening, the movement needed to open the front closure is more than that for the intermediate closure, e.g. by having a front plug with a longer sealed stroke in its sealing seat than the rear plug.

Where plugs or pistons are used, these may be supplemented by films or foils to assure adequate sealing.

A further proposal or embodiment is that the applicator body, at or immediately downstream of the opening means, has one or more baffle structures or tortuous flow formations to promote mixing of the liquid and the additive material as they pass to the applicator pad.

A container providing two chambers according to any of the proposals or embodiments above is an independent aspect of the present disclosure. Such a container pre-filled with first and/or second materials in the respective chambers is a further independent aspect. So also is a procedure of assembling such a container, including pre-filling of the materials and assembly of the first and second chambers to one another.

Desirably the container is substantially cylindrical or has a substantially cylindrical main body part. Where an insert chamber is used, this may fit inside a main wall of the main container without a corresponding enlargement. In known manner a cylindrical container can fit closely into a corresponding tubular guide portion of the applicator body leading to the opening means.

The opening means, e.g. fixed internal structure of the applicator body, can be formed integrally within this tubular receiving or guide structure. Downstream of the opening means there is desirably an antechamber in which the mixed materials can accumulate upstream of the permeable applicator pad. The applicator body desirably provides a rigid flange or support portion to which the permeable pad is secured. However the form of the permeable pad and its mounting is not critical in the present invention and may be in accordance with any known proposals.

Desirably a flow distributor element is positioned over the back surfaces of the pad to moderate and distribute the liquid flow into the pad. This may be in accordance with the disclosure of our co-pending PCT application also filed 10 Aug.

2010 and entitled "APPLICATORS", reference GPS/BP6705032, the entire contents of which are incorporated herein by reference.

The applicator may include a vent opening communicating into the flow space between the back surface of the permeable pad and the front opening position for the container. This helps smooth emptying of the container, which is usually closed at the rear.

BRIEF DESCRIPTION OF THE DRAWINGS

Embodiments of the proposals are now described by way of example, with reference to the accompanying drawings in which.

DESCRIPTION OF THE SELECTED EMBODIMENTS

Figure 1:
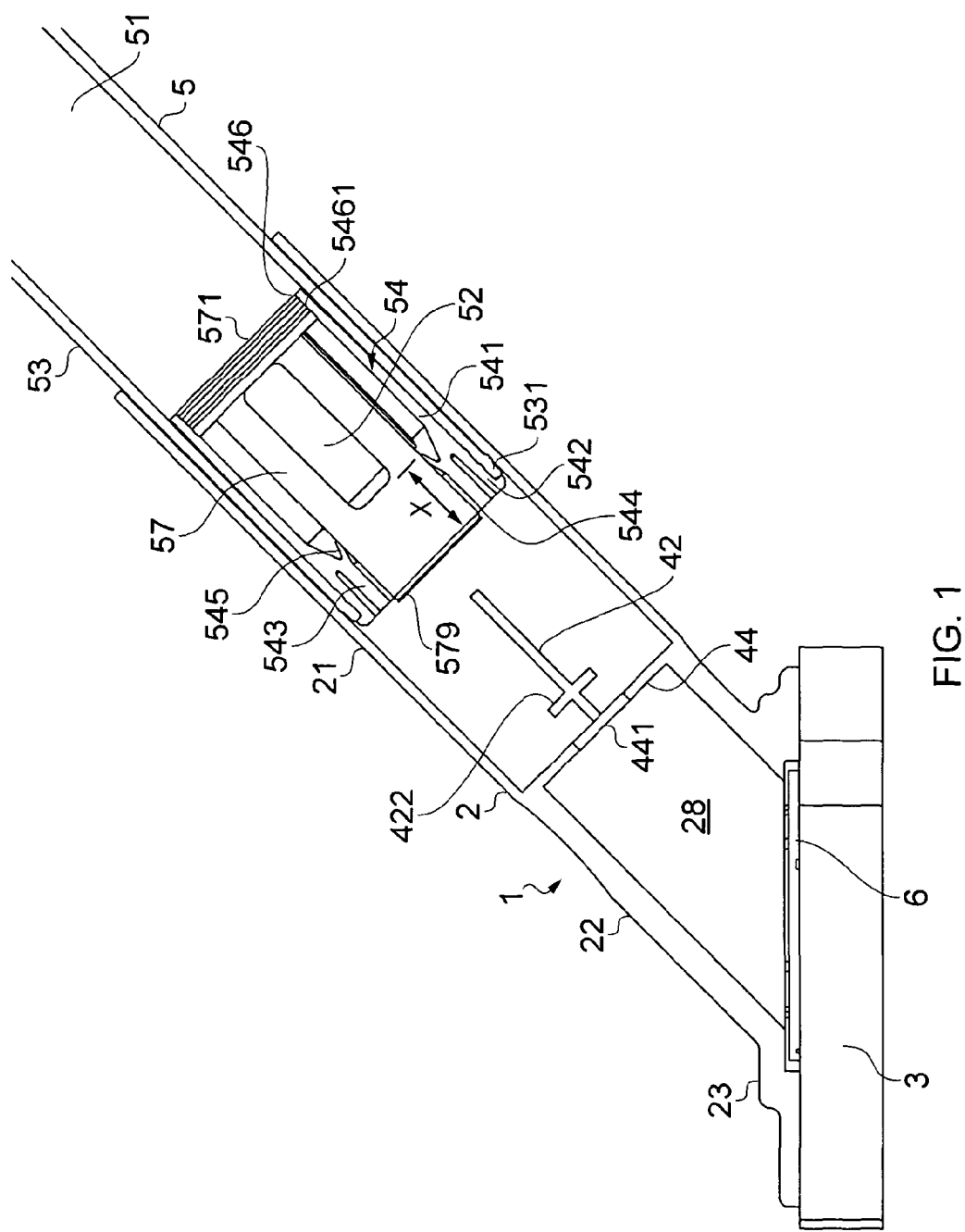
FIG. 1 is an axial section showing the front part of a first embodiment of an applicator according to this disclosure.

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates. One embodiment of the invention is shown in great detail, although it will be apparent to those skilled in the relevant art that some features that are not relevant to the present invention may not be shown for the sake of clarity.

With reference to FIGS. 1 to 4, a surgical pre-prep applicator takes a generally known form with a plastics applicator body unit 1 having a generally tubular casing 2 which receives a cylindrical cartridge 5 of disinfectant liquid having a special construction, described later. The applicator body 1 also includes a front open tubular portion 22 enclosing an antechamber 28, and a front flange 23 on the front of which an applicator pad 3 is fixed. The elliptical front opening of the antechamber 28 faces downwardly onto the top face of the pad 3, where an impermeable flow distributor disc 6 is held to distribute liquid over the pad. This distributor disc 6 embodies ideas described in our above-mentioned co-pending application.

A rear cylindrical part of the applicator body 2 constitutes a guide casing or receiving portion 21 for the disinfectant cartridge 5, which slides into it with a close fit. Between the receiving portion 21 and the antechamber 28, a container-opening structure 42 is provided in the body 2, here in the form of an axially-extending central rearward projection directed onto the front of the cartridge 5. It may have a cross or star cross-section for rigidity. Immediately downstream of the opening formation 42 a partition 44 with a central hole 441 spans the tube interior. A circular baffle element 422 near the bottom of the opening structure 42 is aligned axially immediately upstream of the hole 441. Thus, liquid which flows from the cartridge must flow around the circular baffle 422 and then inwardly to pass through the hole 441, promoting mixing of components.

The cartridge 5 is now described in more detail. It contains a main volume of disinfectant liquid in a rear chamber 51 and a small volume of a dye or other additive in a front chamber 52. The entire cartridge has a generally cylindrical outer casing 53 with an open front end or mouth 531. The disinfectant liquid may be of any suitable kind.

A chamber insert 54 is plugged into the mouth 531 of the main cartridge tube 53, held in place by snap ribs adjacent the mouth, and closes it off as seen in the figures. The chamber insert comprises an outer sleeve or shell 541, a one-piece plastics unit which is open at both ends. Its front end has outward snap formations 542 which lock into the mouth of the main tube 53, and a concentric inner sleeve portion 543 carrying a sealing lip 545 at its rear edge. The sealing lip is spaced by a distance "x" from the front of the sleeve 541. This inner sleeve 543 provides the actual mouth opening 544 of the chamber insert 54.

The rear end of the sleeve 541 has a simple circular opening 546 with small snap grooves 5461 around the inside.

The other main component of the insert 54 is a closure slide or plug member 57. It comprises a rear plug portion 571 with external beads which plug securely into the rear mouth 546 of the insert's sleeve 541. It has a front plug portion 572 with a smooth uniform outer diameter region which fits sealingly through the sealing lip 545 of the inner sleeve segment 543 at the front of the unit, and has a front edge which lies substantially flush with the mouth opening 544 at the front of the unit, and is closed off with a foil or polymeric sealing film 579.

Between these front and rear plugs 572,571 the closure slide 57 has a rigid structure of legs 575 and windows 576, spaced substantially inwardly from the inner wall of the shell 541. In this embodiment the legs 575 are provided as continuations of the tubular wall of the front plug 572, for simplicity and strength. However their only necessary function is to provide a connection between the front and rear plugs which is adequately strong in compression (for pushing out the rear plug) without isolating part of the interior volume. Therefore many arrangements e.g. of single or multiple struts are possible.

Figure 2:
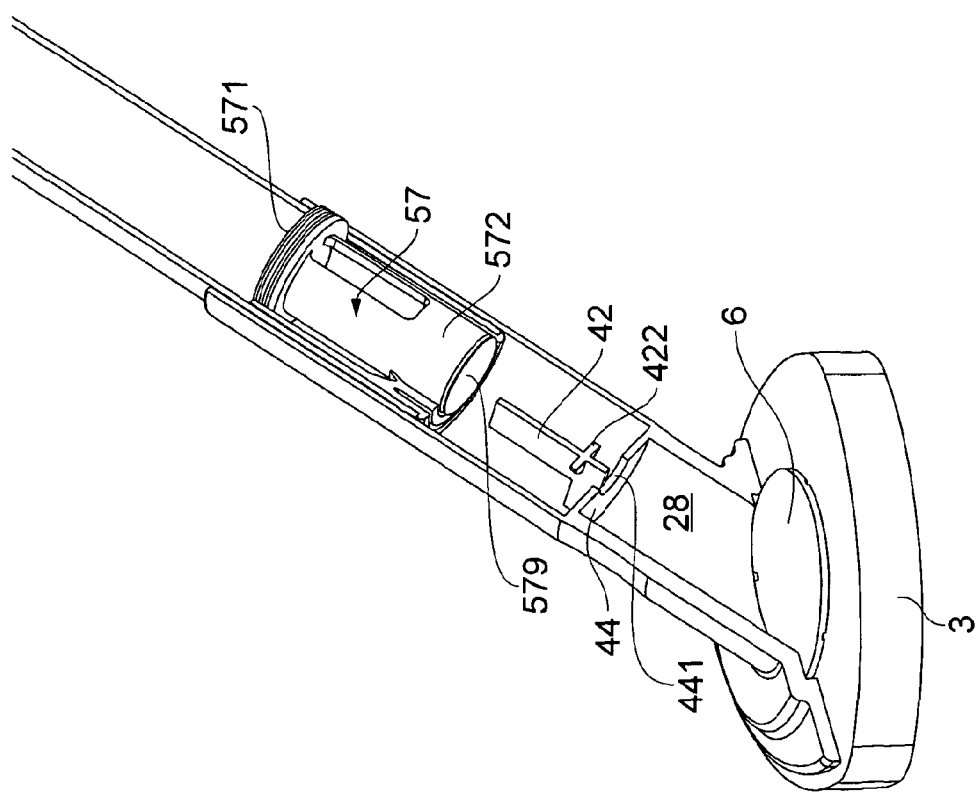
FIG. 2 is an oblique view of the FIG. 1 section, in a first (pre-actuation) position.
Figure 3:
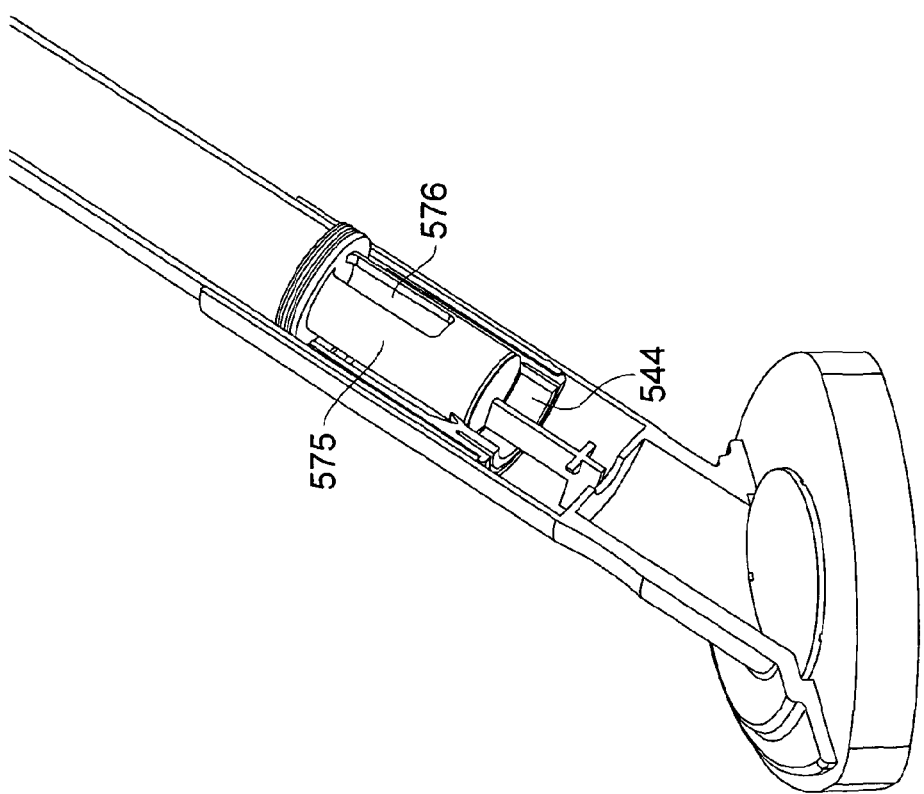
FIG. 3 shows the FIG. 1 applicator at an intermediate stage of actuation.
Figure 4:
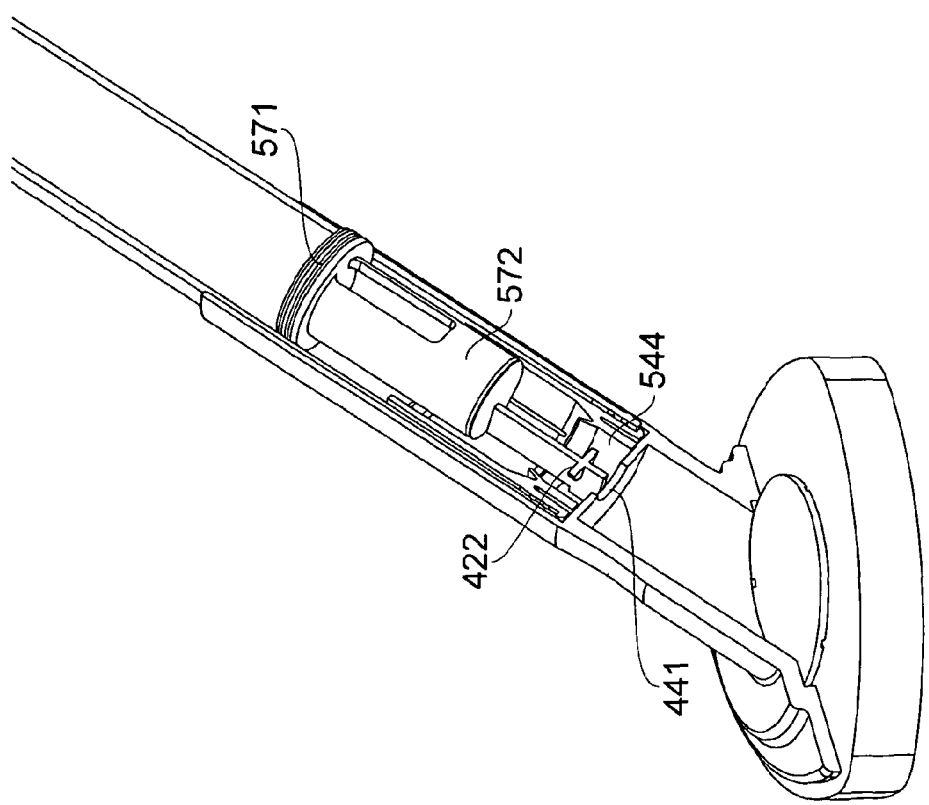
FIG. 4 shows the end of the actuation.

Operation of the device can be understood from FIGS. 2 to 4. To open the container and release its contents, the cartridge 5 is pushed into the applicator guide casing 21. The end of the opening projection 42 meets the front face of the front plug 572 so that, as the cartridge 5 is further advanced, the closure slide 57 is pushed relatively back inside it. With sufficient force this immediately pushes the rear plug 571 out of the back of the shell 541 into the wider region beyond, so that liquid from the main chamber 51 and the contents of the shell 541 (e.g. a dye additive, liquid or solid) can mix. At this time the front plug 572 is still in sealing engagement with the front sealing lip 545, because the distance of displacement has not exceeded "x" indicated in FIG. 1. So, no liquid yet escapes forwardly into the flow path. There is only pre-mixing of the two materials.

Pushing the cartridge 5 as far as possible into the guide casing 21, as shown in FIG. 4, moves the front plug 572 clear of its seal 545 so that the front mouth 544 of the insert chamber 54 is opened and the mixed disinfectant liquid and dye can flow out. Mixing is promoted by the tortuous baffle formations 422,44. The mixed liquid then passes forward to the applicator sponge.

Figure 5:
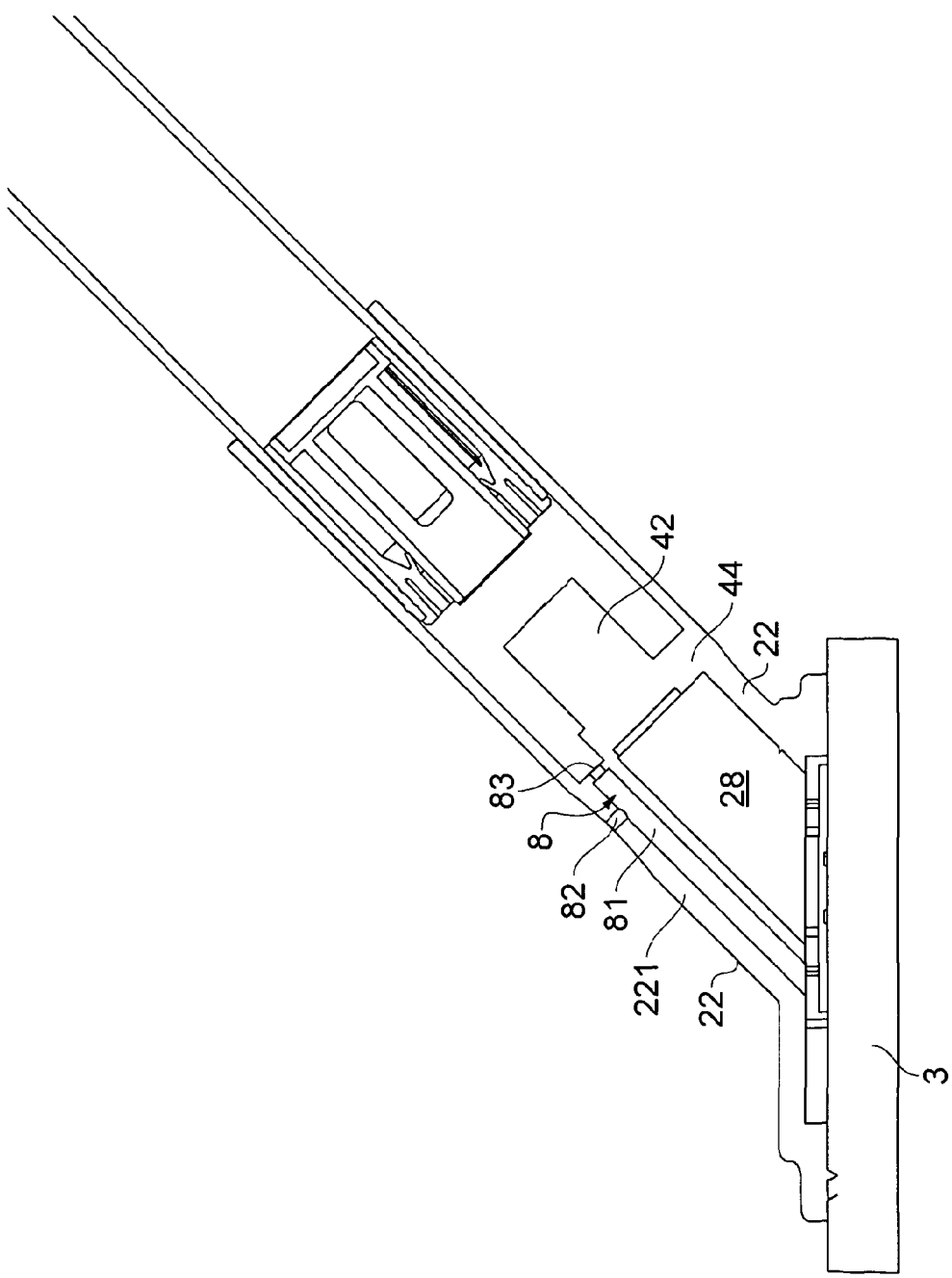
FIG. 5 shows a variant with a vent for the applicator flow path.

FIG. 5 shows a variant in which a vent passage 8 is provided immediately downstream of the open mouth of an opened cartridge. A thicker portion 221 of the surrounding wall accommodates a vent bore 81 so that the vent can be isolated from the antechamber 28. A vent entry hole 82 into the vent bore 81 through the outer shell, and a vent access hole 83 through the partition 44 leads from the vent bore 81 into the space adjacent the container front. The opening structure 42 is shaped to hold the front edge of the cartridge 5 clear of the partition 44, to allow the passage of air. Providing the vent towards the top of the handle prevents liquid leakage there. Any liquid that does fall through the vent access hole 83 can drain down to the sponge pad 3 through the vent bore 81. The provision of a vent, preferably via a vent bore defined in the wall and communicating down to the rear of the applicator pad, is an independent proposal in the present disclosure and is useful with surgical prep applicators of other kinds, e.g. which use a single-chamber cartridge.

Figure 6:
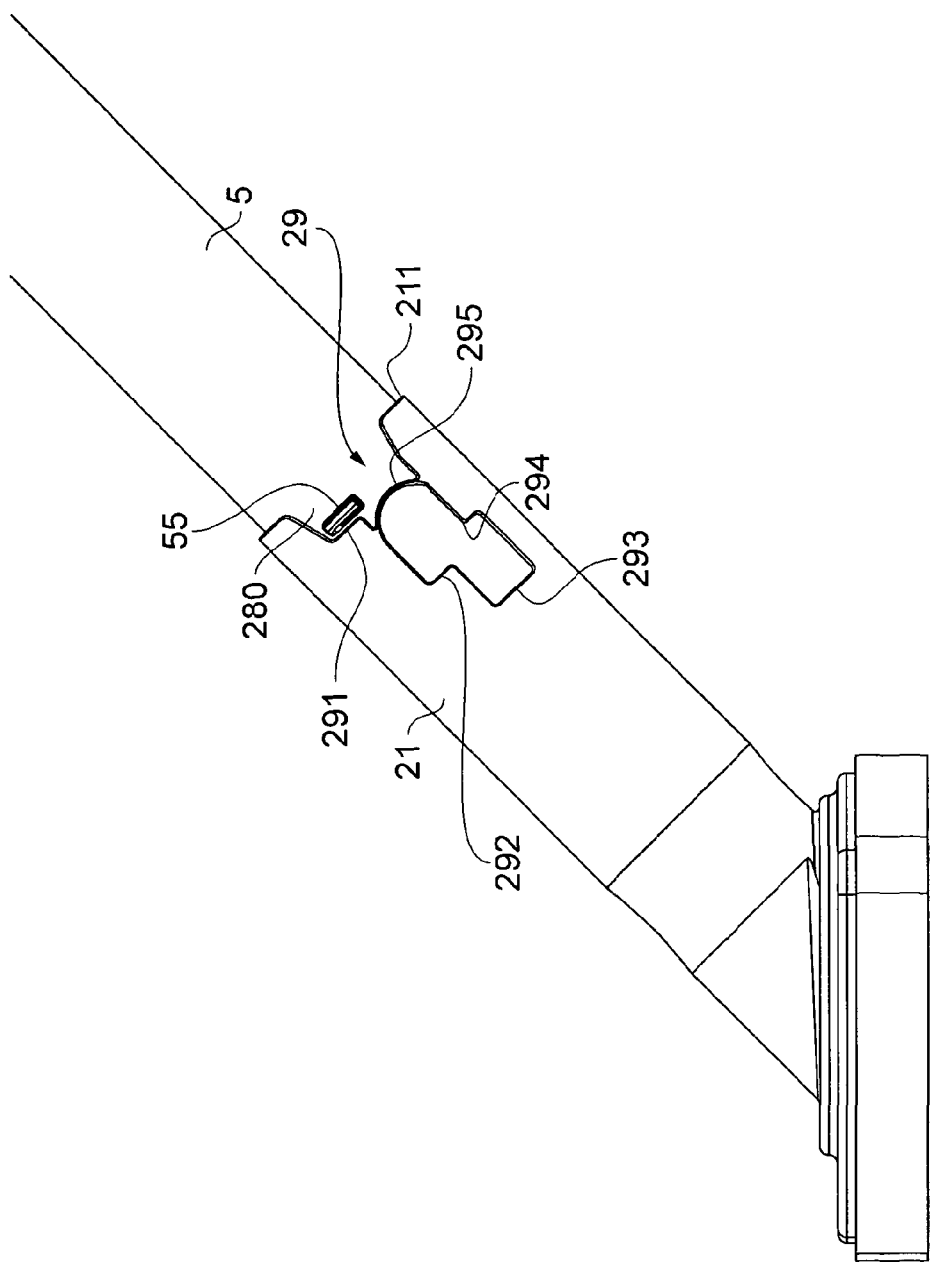
FIG. 6 shows an initial position of guide formations of the applicator body and product container, corresponding to the stages of FIGS. 2 to 4.

Referring to FIG. 6, the top edge 211 of the wall of the guide casing is generally flat except for a specially-shaped notch or track 29 which guides and controls the movement of a lug 55 fixed on the outside of the cartridge 5.

It is important that the cartridge 5 is not pushed in during casual handling or shipping, inadvertently releasing its contents. However it must be simple to push it in when actually needed. We show here a flexible arcuate stopper rib 295 extending across the mouth of the notch at a start level corresponding to initiation of the actuation stroke, to stop accidental initiation of the operating stroke.

Figure 7:
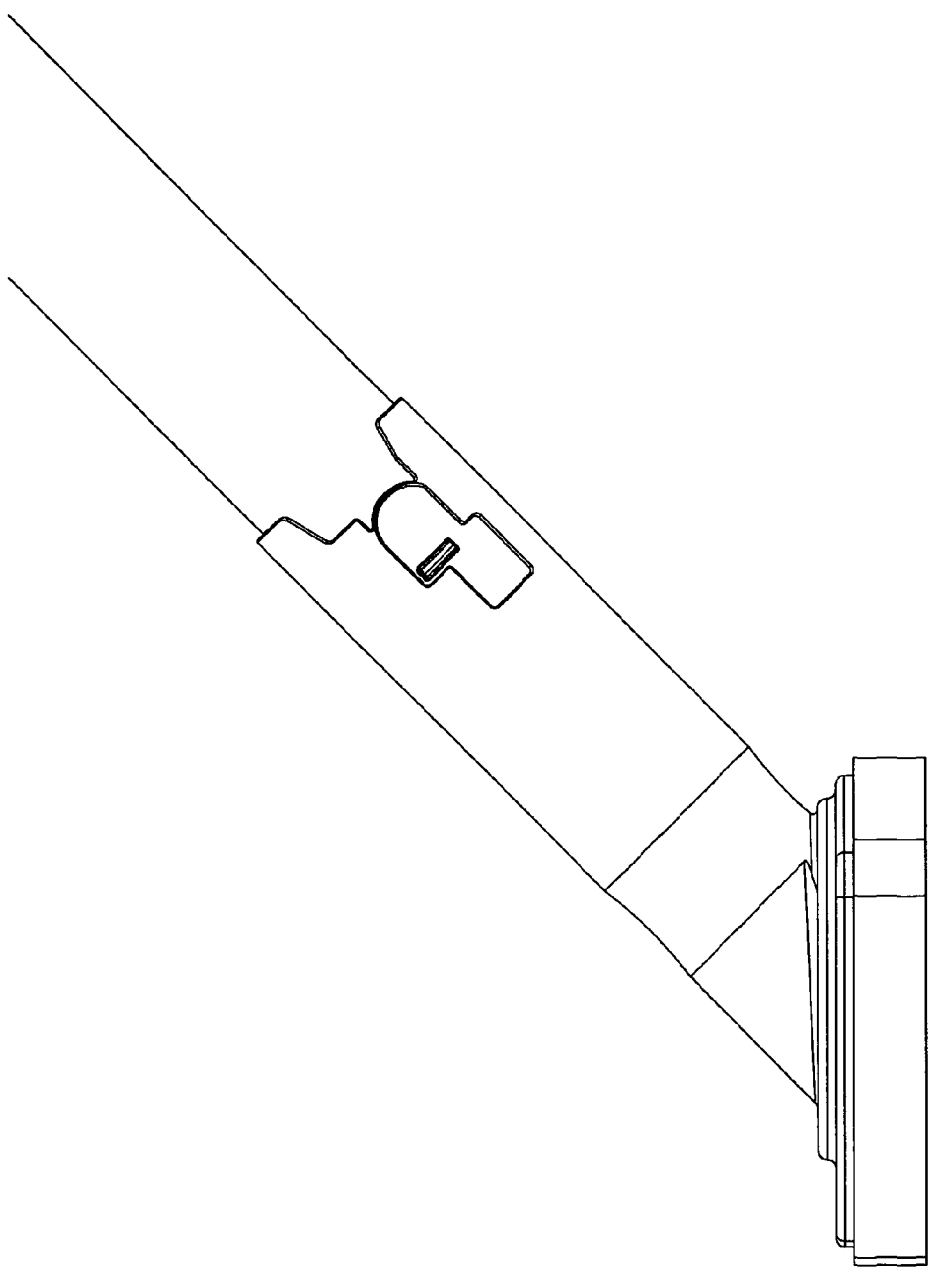
FIG. 7 shows an intermediate position of guide formations of the applicator body and product container, corresponding to the stages of FIGS. 2 to 4.
Figure 8:
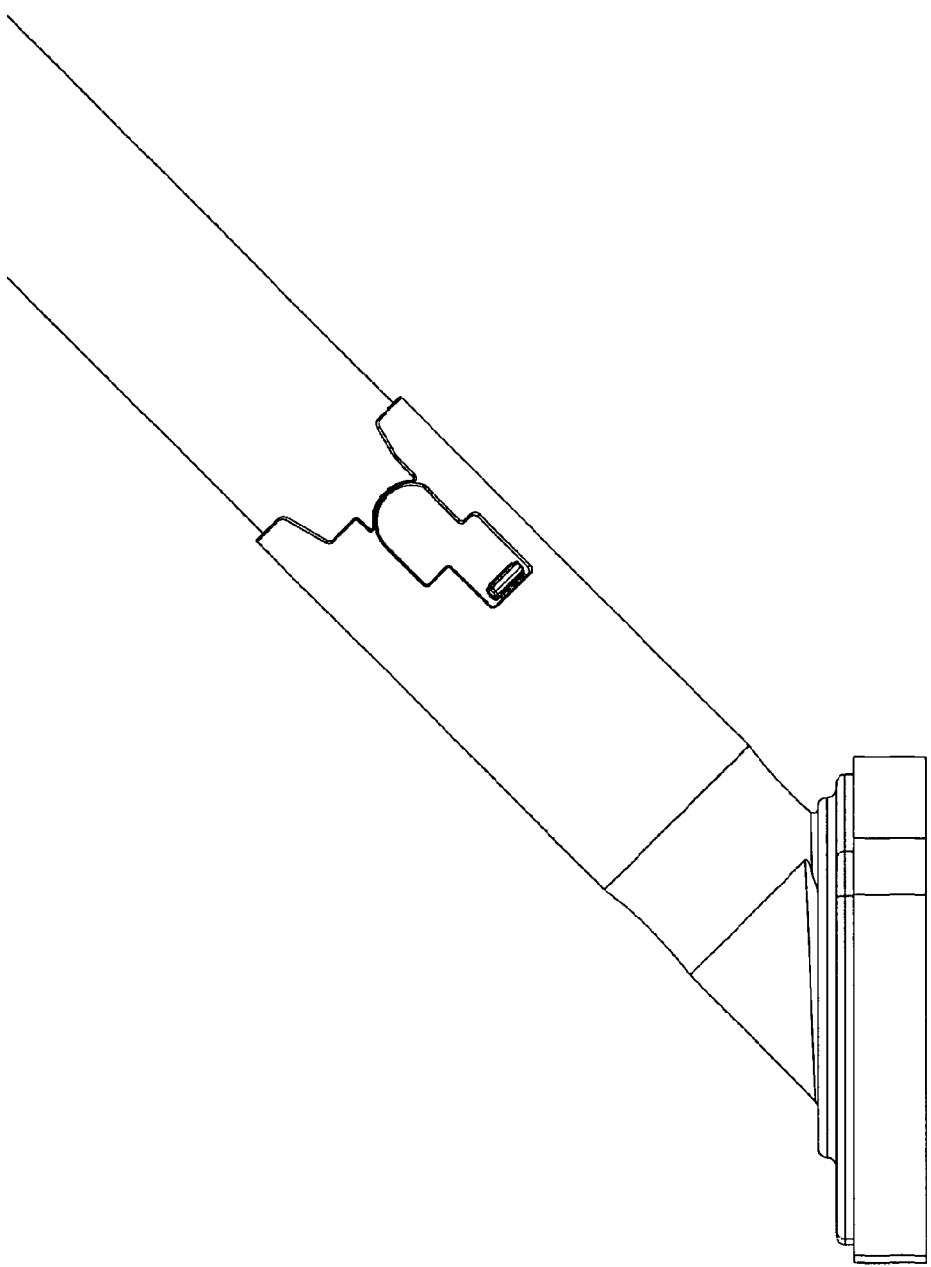
FIG. 8 shows a final position of guide formations of the applicator body and product container, corresponding to the stages of FIGS. 2 to 4.

The notch 29 has a wider entry or guide region 280 above the flexible stopper rib, extending down below the circular edge of the casing 21, to avoid exposing the rib 295 to damage. It also protects the lug from accidental engagements. This entry or guide region 280 includes an abutment or shoulder 291 where the lug 55 can rest without resting against the rib 295. This corresponds to a position as in FIG. 2. To initiate actuation, the cartridge 5 is turned to bring the lug 55 to above the rib 295 and then pushed in hard so that it passes underneath the rib 295, with outward flexion of the latter, and into a first track segment of the track or notch 29. The casing 21 is made of tough strong plastics for necessary general strength, hence the thin curved form of the integral rib so that it can flex. The direct push of the cartridge 5 brings it up against a second abutment shoulder 292 at the end of the first track segment; FIG. 7. This is the FIG. 3 condition with preliminary mixing of dye and disinfectant. After whatever time is desired or necessary for mixing, the user twists the cartridge 5 slightly to carry the lug 55 around the stagger 294 in the track i.e. off the shoulder 292 and down a second track segment onto a final stop 293 (FIG. 8), corresponding to the FIG. 4 position where the cartridge contents are released behind the pad.

With a single-chamber cartridge, or with a two-chamber cartridge whose front and intermediate closures may open at the same time, the two-stage staggered track formation is not relevant but the flexible rib idea, optionally also with the preliminary guide zone of the notch, is generally useful.

Figure 9:
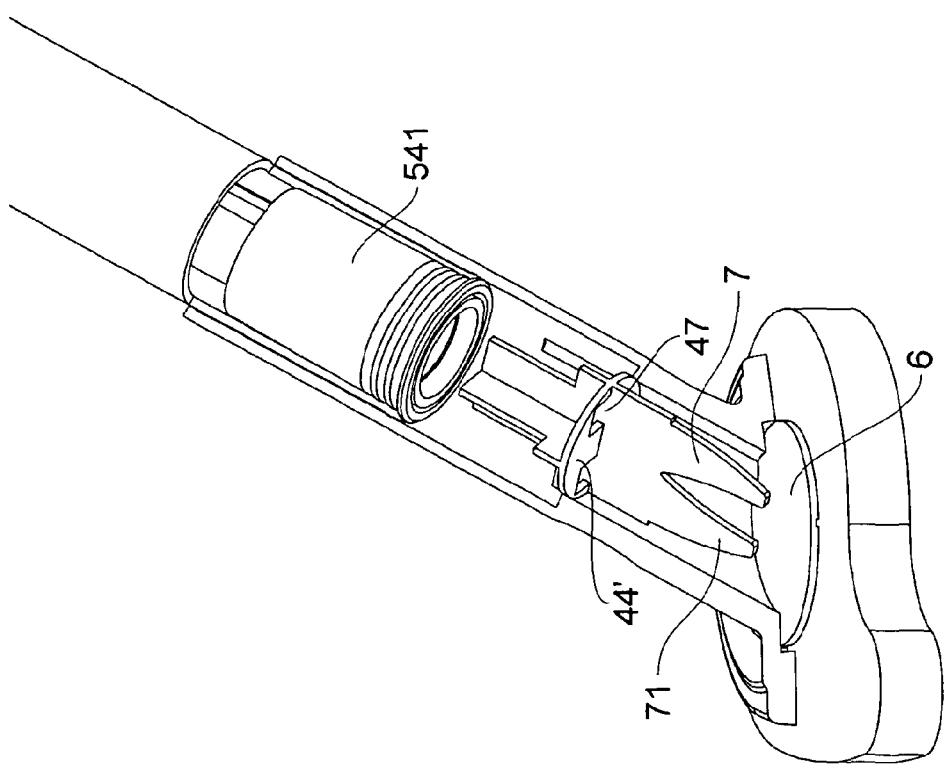
FIG. 9 shows a variant applicator with an internal liquid spreader member.

FIG. 9 shows a variant embodiment (and incidentally, the exterior of the insert chamber 541). To help carry the flow of liquid out to the centre of the distributor disc 6, the partition wall 44 carries a downward spreader tongue 7 with two limbs 71, and has flow openings 47 which are larger above the tongue than below so that much of the liquid must flow over the tongue and fall from its end. This reduces the tendency for much of the liquid otherwise to arrive at the near side of the sponge. Such a spreader tongue may also be used without a distribution element such as disc 6.

Figure 10:
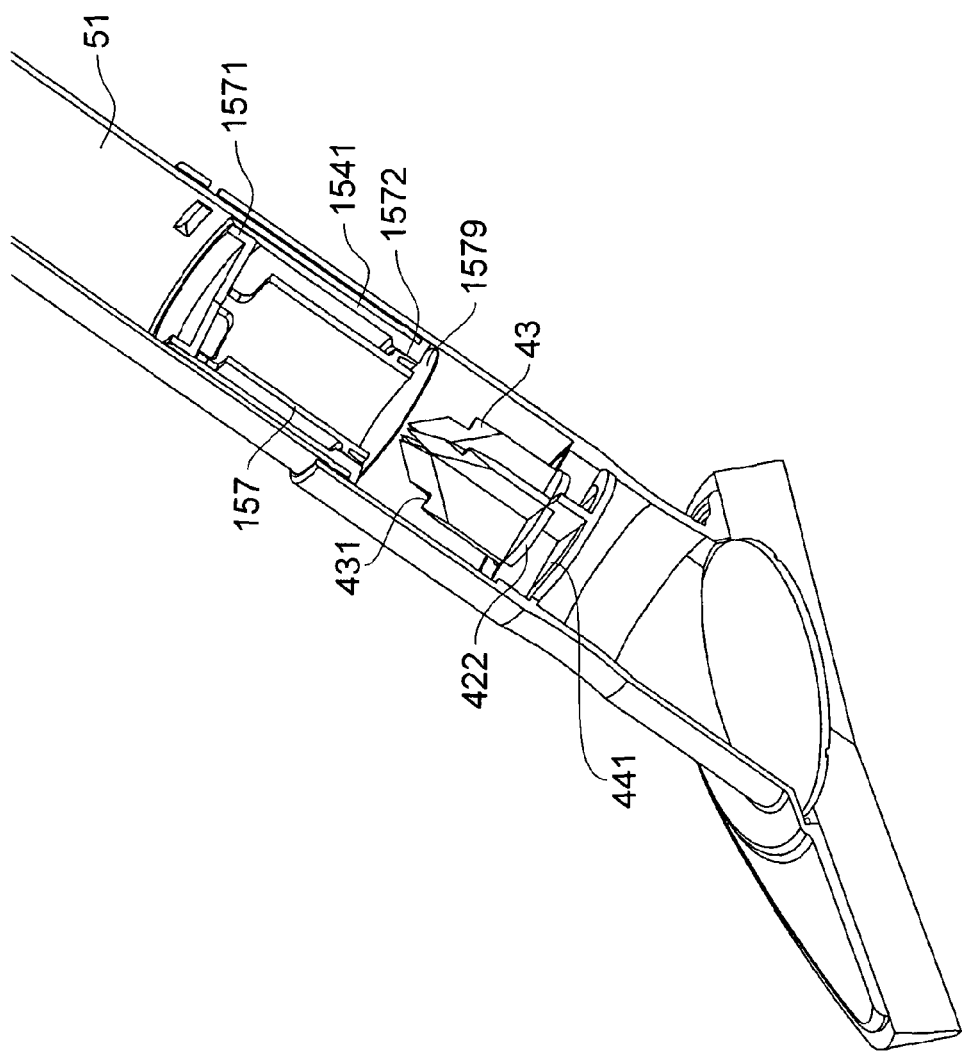
FIGS. 10 to 12 are views, corresponding to those of FIGS. 2 to 4, of a further embodiment at initial, partial and completed actuation positions.
Figure 11:
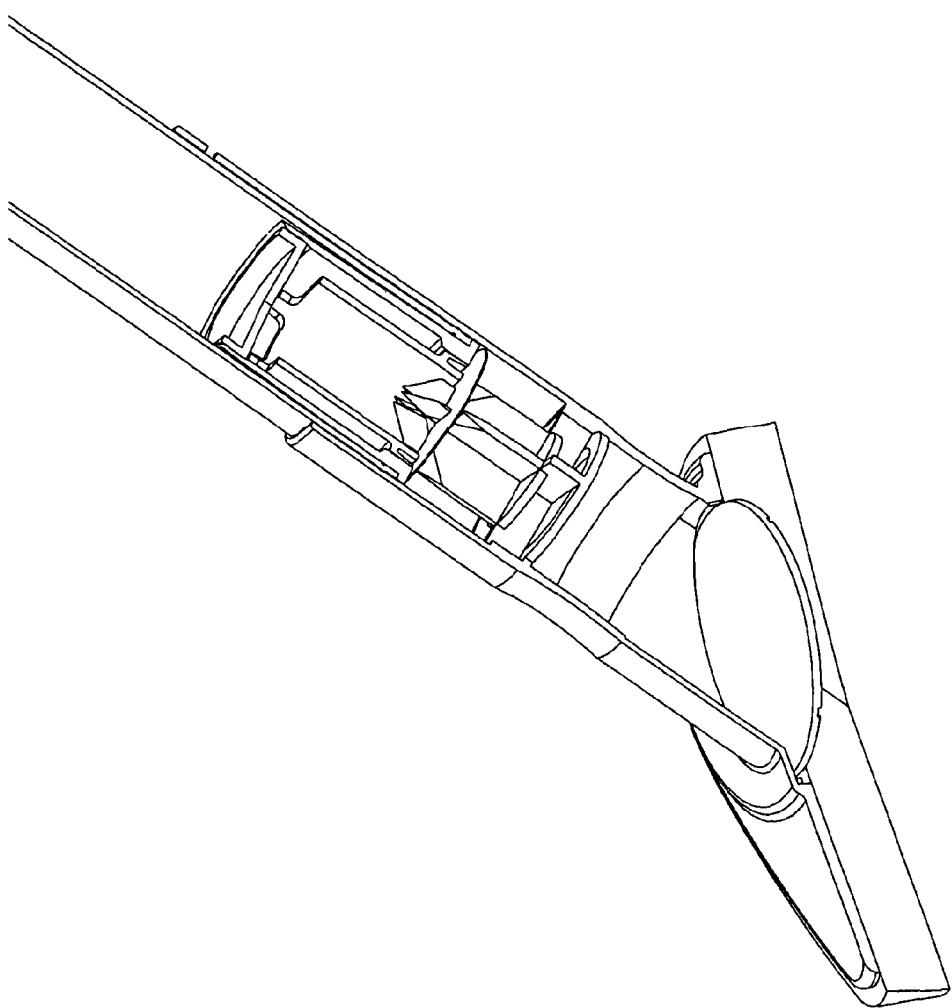
Figure 12:
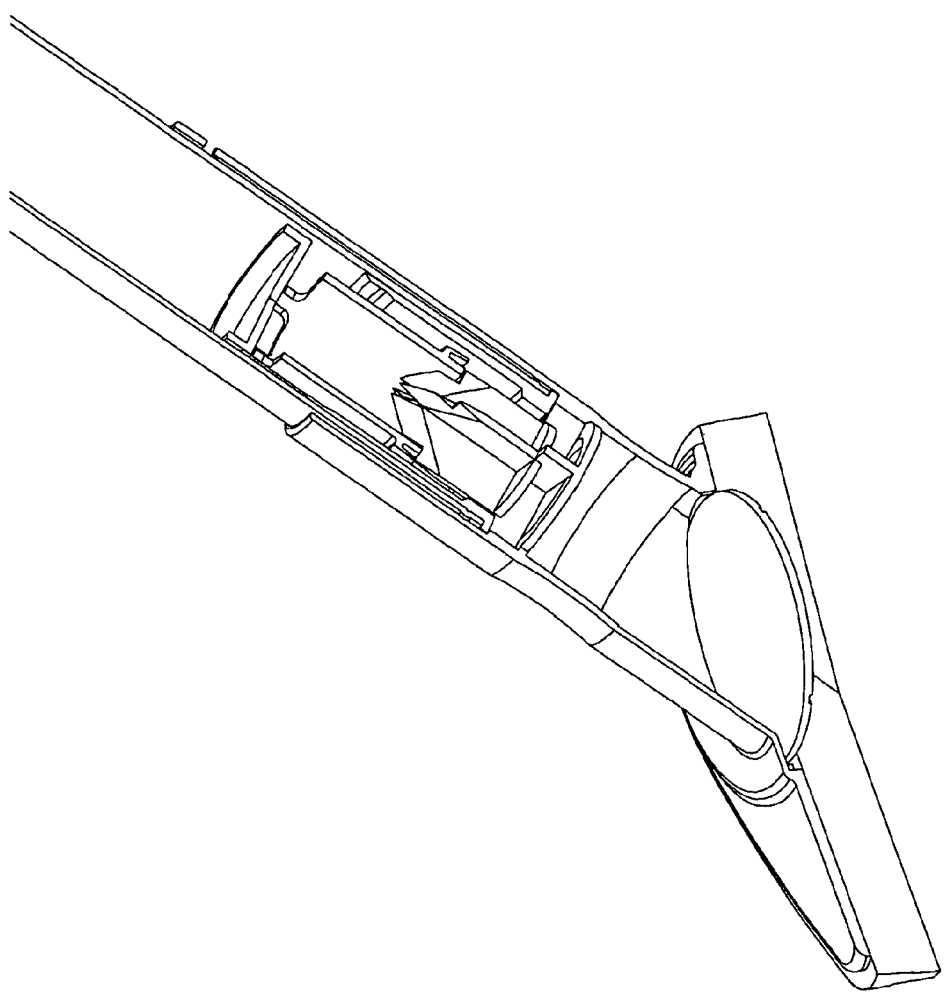

FIGS. 10 to 12 show the initial, intermediate and fully-open conditions (corresponding to FIGS. 2 to 4) for a further embodiment using a combination of cutting and pushing for the opening actions. The opening structure has a cutter 43 with top points and shoulders 431 further down. In the first embodiment the abutment or pusher formation 42 of the opening means did not rupture the film or foil 579, which was used only as a convenient means of sealing the insert, not of opening it. In this embodiment a corresponding film 1579 is applied right across the front of the chamber insert, protecting additionally the sealed sliding join between the front plug 1572 and the outer sleeve 1541.

The initial movement of the cutter 43 breaks through the film 1579 so that dye starts to escape through the front opening: FIG. 11. After this initial stage the shoulders 431 on the cutter engage the inner plug sleeve 157 and push it up, thereby pushing the rear plug 1571 out of its seat and allowing the disinfectant liquid to flow in from the main chamber 51 and out through the front opening to mix with the dye: FIG. 12. A tortuous pathway to promote mixing is provided by a baffle 42 and restricted opening 441 analogous to those in the first embodiment.

This embodiment does not provide the two-stage confined mixing procedure of the first embodiment, so the two-stage external control track need not be used. It illustrates the wide range of possibilities available with the present two-chamber concepts. The skilled reader will understand that various configurations are possible exploiting the ideas described herein. For example the dye could be provided in a small rear chamber, and admitted forwardly to the front main chamber, opening a partition between them by means of an actuator e.g. a plunger or pusher at the back of the cartridge. Another possibility is that the front capsule or chamber containing the dye need not be fitted right inside the mouth of the main cartridge tube, but could instead fit into it only partly, or indeed be separate from it, the dye (additive) chamber and disinfectant (main liquid) cartridge being inserted in sequence. This would call for respective rear and front seals for the front and rear chambers, but these could be ruptured or otherwise opened together by a suitable formation at the rear of a pusher member in the front chamber. The concept can be adapted to operate with various combinations of different kinds of seals or closure elements.

While the invention has been illustrated and described in detail in the drawings and foregoing description, the same is to be considered as illustrative and not restrictive in character, it being understood that only the preferred embodiment has been shown and described and that all changes, equivalents, and modifications that come within the spirit of the inventions defined by following claims are desired to be protected. All publications, patents, and patent applications cited in this specification are herein incorporated by reference as if each individual publication, patent, or patent application were specifically and individually indicated to be incorporated by reference and set forth in its entirety herein.

The invention claimed is:

1. An applicator comprising:
an applicator body;
an applicator pad attached at a front part of the applicator body;
a container of liquid received in a receiving structure of the applicator body, the applicator body defining a flow path for liquid to flow from the container to the applicator pad, the container having a closure portion which is openable to allow liquid to flow from the container into the flow path, the applicator body including an opening member which interacts with the front of the container when the container is moved to an opening position relative to the applicator body to open the openable closure portion; and
wherein the container defines a first chamber and a second chamber with a liquid-impermeable barrier between them, the first chamber having the openable closure portion at its front end and the barrier at its rear end, and
wherein the container includes one or more longitudinal pusher elements extending relatively movably between the ends of the front chamber, whereby operating movement of the opening member acting at the front end to open the openable closure portion is transmitted to the rear end by a follower action of said one or more longitudinal pusher elements to open the barrier.

2. An applicator according to claim 1 in which the closure portion comprises a sliding plug.

3. An applicator according to claim 1 in which the barrier comprises a sliding plug.

4. An applicator according to claim 1 whereby in an operating stroke in which the container moves to the opening position relative to the applicator body, the barrier opens at an intermediate stage of the operating stroke, before the closure portion opens.

5. An applicator according to claim 4 in which the closure portion comprises a plug, slidably movable over a distance long enough for said one or more longitudinal pusher elements to open the barrier while the plug remains sealed.

6. An applicator according to claim 4 in which the closure portion and the barrier comprise respective slidable plugs, connected by one or more longitudinal members constituting said one or more longitudinal pusher elements.

7. An applicator according to claim 1 in which the first chamber is defined in a self-contained insert comprising the barrier and the closure portion, and which is fitted into a main container in which the second chamber is defined behind the front chamber.

8. An applicator according to claim 1 in which the applicator body defines a path and the container has a projection which moves along the path as the container and applicator body are moved relative to one another to the opening position.

9. An applicator according to claim 8 in which the path has an intermediate abutment to interrupt the operating stroke at an intermediate point.

10. A surgical prep applicator comprising
an applicator body;
an applicator pad attached at a front part of the applicator body;
a pre-loaded container of liquid slidably received in a tubular receiving structure of the applicator body, the applicator body defining a flow path for liquid to flow from the container to the applicator pad, the container having a front end with an openable front closure portion which when opened allows liquid to flow from the container into the flow path, the applicator body including opening means having a projecting formation which interacts with the front of the container when the container is moved to an opening position relative to the applicator body, in an operating stroke which is a push of the container into the applicator body, to open the openable front closure portion; and
wherein the openable front closure portion of the container includes a front opening of the container which defines a sealing seat and a displaceable plug which fits in the sealing seat to close the front opening, and wherein the projecting formation is a projecting pusher formation, the displaceable plug being engageable by said projecting pusher formation in the operating stroke to slide the displaceable plug rearwardly out of the sealing seat in the front opening of the container, to create an opening for forward flow of the surgical prep liquid out of the container and into the flow path around the projecting pusher formation.

11. An applicator comprising:
an applicator body;
an applicator pad attached at a front part of the applicator body;
a container of liquid received in a receiving structure of the applicator body, the applicator body defining a flow path for liquid to flow from the container to the applicator pad, the container having a closure portion which is openable to allow liquid to flow from the container into the flow path, the applicator body including an opening structure which interacts with the front of the container when the container is moved to an opening position relative to the applicator body to open the openable closure portion; and
wherein the receiving structure of the applicator body defines a track, and the container received in the applicator body has a projection which moves in said track on movement of the container from an initial position to an opening position at which the closure portion thereof is opened by interaction with the opening structure of the applicator body, and wherein the receiving structure of the applicator body includes an abutment extending across a mouth of the track at a start level thereof, corresponding to initiation of the actuation movement, whereby to enter the track the projection on the container must be pushed past said abutment.

12. An applicator according to claim 11 wherein said abutment is a flexible stopper rib.

13. An applicator according to claim 12 in which the receiving structure for the applicator body defines a wider entry region above the flexible stopper rib, including a structure where the projection can rest without resting against the rib.

14. The surgical prep applicator according to claim 10 which the container is closed at the rear and the applicator body has a vent opening communicating into the flow path between the front opening of the container and the applicator pad.

15. The surgical prep applicator according to claim 10 in which the front closure portion comprises a film or foil seal to supplement the sealing by the displaceable plug.

16. The surgical prep applicator according to claim 10 in which the applicator body defines a path and the container has a projection which moves along the path as the container and applicator body are moved relative to one another in the operating stroke to the opening position.

17. An applicator comprising:
an applicator body;

an applicator pad located at one end of the applicator body, said applicator body defining a flow passage to said applicator pad;
a container constructed and arranged with a first chamber containing a first liquid and a second chamber containing a second liquid, said container having a flow barrier positioned between the first chamber and the second chamber, said container received in the applicator body and being movable therein, said first chamber including a flow opening which is openable by movement of said container; and
an opening member constructed and arranged to engage said first chamber, wherein movement of said container toward said opening member results in the opening of said flow barrier allowing flow of said second liquid from said second chamber into said first chamber and wherein with continued movement of said container, the flow opening is opened and said first and second fluids are able to flow from said first chamber via said flow passage to said applicator pad.

18. An applicator comprising:
an applicator body;
an applicator pad located at one end of the applicator body, said applicator body defining a flow passage to said applicator pad;
a container constructed and arranged with a first chamber with a first liquid and a second chamber with a second liquid, a portion of said container being received within said applicator body for axial movement therein, said container being rotationally movable relative to said applicator body;
an opening member positioned between said container and said applicator pad, wherein axial movement of said container toward said opening member releases said first and second liquids for flow to said applicator pad; and
said container including an abutment member which in a first position prevents said axial movement and said container being rotatable to a second position wherein said axial movement is permitted.

19. The applicator of claim 18 wherein said container includes a seal closing off one end of said container.

20. The applicator of claim 19 wherein said opening member being constructed and arranged to penetrate said seal for the release of liquid from at least one of said first and second chambers.

21. The applicator of claim 20 wherein said container includes a barrier positioned between said first chamber and said second chamber.

22. The applicator of claim 21 wherein said abutment member is a projection.

23. The applicator of claim 22 wherein said first position is a locked position with said projection extending over an edge of said applicator body.

24. An applicator comprising:
an applicator body;
an applicator pad located at one end the applicator body, said applicator body defining a flow passage to said applicator pad, and said applicator body defining a liquid exit hole;
a container constructed and arranged with a first chamber with a first liquid and a second chamber with a second liquid;
an opening member positioned between said container and said applicator pad, wherein movement of said container toward said opening member releases said first and second liquids for flow to said applicator pad; and
said opening member being constructed and arranged to create a tortuous flow path for liquid prior to reaching said liquid exit hole.

25. The applicator of claim 24 wherein said container includes a seal closing off one end of said container.

26. The applicator of claim 25 wherein said opening member being constructed and arranged to penetrate said seal for the release of liquid from at least one of said first and second chambers.

27. The applicator of claim 26 wherein said container includes a barrier positioned between said first chamber and said second chamber.

28. The applicator of claim 24 wherein a portion of said container being received within said applicator body for axial movement therein, said container being rotationally movable relative to said applicator body.

29. The applicator of claim 28 wherein said container including an abutment member which in a first position prevents said axial movement and said container being rotatable to a second position wherein said axial movement is permitted.

* * * * *